United States Defensive Publication [19] (H) [11] T964,006
Bailey et al. [43] Nov. 1, 1977

[54] ANTIMICROBIAL FATTY ESTER-AMIDES

[76] Inventors: August V. Bailey, 4470 San Marco Road, New Orleans, La. 70129; Gordon J. Boudreaux, 6625 Dorian St., New Orleans, La. 70126; Gene Sumrell, 1540 Aviators St., New Orleans, La. 70122; Arthur F. Novak, 656 College Hill Drive, Baton Rouge, La. 70808

[21] Appl. No.: 768,808

[22] Filed: Feb. 15, 1977

Related U.S. Application Data

[62] Division of Ser. No. 667,063, March 15, 1976, Pat. No. 4,017,522.

[51] Int. Cl.[2] ..... C09F 5/00
[52] U.S. Cl. ..... 260/404; 424/285; 424/308; 424/312

[57] ABSTRACT

New ester-amides containing one or more long chain fatty acyl groupings are described which have antimicrobial activity against several pathogenic microorganisms, and have properties making them useful as antimicrobial agents.

20 Claims, No Sheets Drawing,

15 Pages Specification

The file of this unexamined application may be inspected and copies thereof may be purchased (849 O.G. 1221, Apr. 9, 1968).